United States Patent
Squadrito

(10) Patent No.: US 9,486,438 B2
(45) Date of Patent: *Nov. 8, 2016

(54) COMBINATION DOSAGE FORMS AND THERAPIES FOR SUPPORTING BONE HEALTH

(71) Applicant: Primus Pharmaceuticals Inc., Scottsdale, AZ (US)

(72) Inventor: Francesco Squadrito, Messina (IT)

(73) Assignee: Primus Pharmaceuticals, Inc., Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/661,555

(22) Filed: Mar. 18, 2015

(65) Prior Publication Data
US 2015/0190365 A1 Jul. 9, 2015

Related U.S. Application Data

(63) Continuation of application No. 13/684,725, filed on Nov. 26, 2012, now Pat. No. 9,066,921, which is a continuation of application No. 12/409,090, filed on Mar. 23, 2009, now Pat. No. 8,338,393.

(60) Provisional application No. 61/038,792, filed on Mar. 24, 2008.

(51) Int. Cl.
| | |
|---|---|
| *A61K 31/352* | (2006.01) |
| *A61K 31/315* | (2006.01) |
| *A61K 31/593* | (2006.01) |
| *A61K 33/06* | (2006.01) |
| *A61K 33/30* | (2006.01) |
| *A61K 45/06* | (2006.01) |

(52) U.S. Cl.
CPC ........... *A61K 31/352* (2013.01); *A61K 31/315* (2013.01); *A61K 31/593* (2013.01); *A61K 33/06* (2013.01); *A61K 33/30* (2013.01); *A61K 45/06* (2013.01)

(58) Field of Classification Search
USPC ........................................................ 514/183
See application file for complete search history.

(56) References Cited

U.S. PATENT DOCUMENTS 5,935,996 A 8/1999 Yamaguchi

OTHER PUBLICATIONS

Ensrud et al., "Randomized trial of effect of alendronate contination versus discontinuation in women with low BMD: Results from the fracture intervention trial long-term extension" J Bone Miner Res (2004) vol. (19(8) pp. 1259-1269.
Morabito et al. "Effects of Genistein and Hormone-Replacement Therapy on Bone Loss in Early Postmenopausal Women: A Randomized Double-Blind Placebo-Controlled Study." J Bone Miner (Res) (2002) vol. 17 pp. 1904-1912.
Grant et al. "Benefits and Requirements of Vitamin D for Optimal Health: A Review." Altern Med Rev (2005) vol. 10 (2) pp. 94-111.
Cooper et al. "Vitamin D supplementation and bone mineral density in early postmenopausal women." Am J Clin Nutr (2003) vol. 77 pp. 1324-1329.
Tuppurainen et al. "Does Vitamin D. Strengthen the Increase in Femoral Neck BMD in Osteoporotic Women Treated with Estrogen?" Osteoporos Int (1998) vol. 8 pp. 32-38.
Hollick, M.F. "Vitamin D: Importance in the prevention of cancers, type I diabetes, heart disease, and osteoporosis," Am J Clin Nutr (2004) vol. 79 pp. 362-371.
Griffin, M.D. et al. "Vitamin D and its Analogs as Regulators of Immune Activation and Antigent Presentation." Annu Rev Nutr (2003) vol. 23 pp. 117-145.
Zeitz U. et al. "Impaired insulin secretory capacity in mice lacking a functional vitamin D receptor." FASEB J (2003) vol. 17 pp. 509-511.
Sigmund C.D. "Regulation of rennin expression and blood pressure by vitamin D3." J Clin Invest (2002) vol. 110 pp. 155-156.

*Primary Examiner* — Kathrien Cruz
(74) *Attorney, Agent, or Firm* — Clark G. Sullivan

(57) ABSTRACT

Combined therapies and oral dosage forms based on genistein for the support of osteoporotic health.

9 Claims, 2 Drawing Sheets

COMBINATION DOSAGE FORMS AND THERAPIES FOR SUPPORTING BONE HEALTH

CROSS-REFERENCE TO RELATED APPLICATIONS

The present application is a continuation of U.S. application Ser. No. 13/684,725 filed Nov. 26, 2012, currently pending, which is a continuation of U.S. application Ser. No. 12/409,090, filed Mar. 23, 2009, granted as U.S. Pat. No. 8,338,393, which claims the benefit of U.S. Provisional Application No. 61/038,792 filed Mar. 24, 2008. The disclosure of the foregoing applications is hereby incorporated by reference.

FIELD OF THE INVENTION

The present invention relates to therapies for supporting men's and women's health, and to combination dosage forms that are useful in such therapies. The invention has particular application to post-menopausal women, and to the sustenance and enhancement of bone health among individuals with osteopenia or osteoporosis, as well as to individuals who have drug or lifestyle induced bone loss.

BACKGROUND OF THE INVENTION

Menopause is associated with an increased risk for a number of medical conditions, including osteoporosis, hot flushes and compromised endothelial function. Currently available treatments for postmenopausal osteoporosis include hormone replacement therapy, calcitonin, bisphosphonates and the selective estrogen receptor modulator, raloxifene.

Unfortunately, these treatments suffer from a number of drawbacks. For example, hormone replacement therapy is associated with an increased risk of breast, endometrial and ovarian cancer, cardiovascular disease, venous thromboembolism and stroke. Bisphosphonates are a front line therapy against osteoporosis, but can cause tremendous esophogeal and gastrointestinal complications, and have been associated with the development of osteonecrosis of the jaw. In addition, the efficacy of bisphosphonates may plateau after chronic use, despite ongoing bone loss, as shown by Ensrud et al. (J Bone Miner Res. 2004; 19(8):1259-69) who reported that alendronate provides no benefit at reducing fractures beyond 5 years of treatment. The reason for this bone loss is the degradation of the body's ability to make new bone, known as bone formation.

Genistein is an aglycone phytoestrogen found in soy and soy products. From epidemiological studies, it has been credited with a number of beneficial health effects in Asian populations including reduced risk of fracture and breast cancer and a lowered risk of cardiovascular dysfunction. Genistein is classified as an isoflavone and it structurally resembles 17-beta estradiol, although its pharmacological profile is somewhat different from that of endogenous estrogens. Highly purified genistein aglycone from soy has undergone testing in preclinical and randomized clinical trials to ascertain its effects on bone health, menopausal symptoms, and cardiovascular function. Morabito et al. (2002) reported the results of a study in which genistein administered for one year to post-menopausal women was shown to improve bone mineral density as well as several biochemical markers of bone health. (Morabito et al., J Bone Miner Res. 2002; 17:1904-12).

Dietary supplements have also been proposed for the maintenance of osteoporotic health, including zinc, vitamin D3, vitamin K, and calcium. Yamaguchi et al. have published several articles and obtained at least one United States patent demonstrating a synergistic relationship between genistein and zinc against various markers of bone metabolism. See U.S. Pat. No. 5,935,996.

Vitamin D3 deficiency is known to cause or contribute to several bone diseases including: Rickets, a childhood disease characterized by impeded growth, and deformity, of the long bones; Osteomalacia, a bone-thinning disorder that occurs exclusively in adults and is characterized by proximal muscle weakness and bone fragility; and Osteoporosis, a condition characterized by reduced bone mineral density and increased bone fragility. (Grant et al., Altern Med Rev 2005; 10 (2): 94-111) As a consequence, much has been written about the importance of vitamin D3 for bone health, but there has been little conclusive evidence concerning its effectiveness in supporting bone health in patients who are not deficient in the vitamin.

Several studies have concluded that vitamin D3 has no effect when combined with other agents such as the bisphosphonates or hormone replacement therapy. Cooper et al., in Am J Clin Nutr 2003; 77(5) 1324-1329, reported that in younger postmenopausal women (age: 56 y), whose average vitamin D3 metabolite concentration was well within the normal range, the addition of 10 000 U vitamin D3/wk to calcium supplementation at 1000 mg/d did not confer benefits on bone mineral density beyond those achieved with calcium supplementation alone. Tuppurainen et al., in Osteoporos Int. 1998; 8(1):32-8, reported that there were no statistically significant improvement in lumbar or femoral bone mineral density changes when vitamin D3 was added to estrogen therapy. Therefore, there appears to be little additional benefit to supplemental vitamin D3 once a threshold serum concentration is achieved.

Nevertheless, the literature is replete with suggestions that vitamin D3 assists in various metabolic functions, including helping to maintain calcium balance (Holick M F, Am J Clin Nutr. 2004; 79(3):362-371), as an aid to cell differentiation (Id.), a booster for the immune system (Griffin M D et al., Annu. Rev. Nutr. 2003; 23:117-145), insulin secretion (Zeitz U et al., FASEB J. 2003; 17(3):509-511), and blood pressure regulation (Sigmund C D, J Clin Invest. 2002; 110(2):155-156). All of these metabolic functions can become compromised as a person ages, and would benefit from vitamin D3 supplementation.

SUMMARY OF THE INVENTION

What is needed is a combination dosage form that combines the beneficial properties of genistein with vitamin D3 in a single dosing regimen or multi-component product. However, studies undertaken by these inventors have shown an antagonistic relationship between vitamin D3 and genistein when administered concomitantly. In particular, these inventors have discovered that vitamin D3 can reduce the effectiveness of genistein—EXCEPT when the amounts of genistein and vitamin D3 are carefully controlled, and confined to a discreet range of weight ratios. Therefore, in a first principal embodiment the invention provides a method of providing genistein and vitamin D3 supplementation to a host in need thereof, so that the effectiveness of the genistein is not compromised, comprising orally administering genistein and vitamin D3, wherein the quantity of vitamin D3 is effective to provide vitamin D3 supplementation, but does not compromise the effectiveness of the genistein.

The ratio of genistein to vitamin D3 preferably ranges from about 50:1000 to about 200:1000 (mg:IU), from about 50:1000 to about 150:1000 (mg:IU), or about 135:1000 (mg:IU). The most pronounced effect is observed within these ratios when the genistein is administered at a dose of about 54 mg/day.

As discussed in the background of this document, there are basically two mechanisms of action by which bone mineral density is increased: (1) increased formation of new bone, and (2) decreased resorption of old bone. It is believed that the ratios described herein have their beneficial effect because of their tendency to favor new bone formation over decreased bone resorption. This tendency to favor new bone formation over decreased bone resorption can be measured numerically by, for example, comparing the relative increase or decreases in one or more biochemical markers of bone resorption and bone formation, such as soluble receptor activator of nuclear factor kappaB ligand (sRANKL) and C-terminal telopeptide (CTX) (bone resorption), and bone-specific alkaline phosphatase and osteoprotegerin (OPG) (bone formation), measured as the percentage change from a basal baseline. For example, the treatment preferably increases bone specific alkaline phosphatase over baseline, over the course of twelve months of treatment, by more than 5, 10, 15, 20 or even 25%. The treatment preferably increases insulin-like growth factor-1 over baseline, over the course of twelve months of treatment, by greater than 5, 10 or 15%. The treatment preferably decreases pyridinolone over baseline, over the course of twelve months of treatment, by greater than 4, 8 or 12%. The treatment preferably decreases deoxypyridinoline over baseline, over the course of twelve months of treatment, by more than 4, 8 or 10%.

Therefore, in another embodiment, the invention provides a method of providing genistein and vitamin D3 supplementation to a host in need thereof, comprising orally administering genistein and vitamin D3, wherein the ratio of genistein to vitamin D3 favors new bone formation over the inhibition of old bone resorption, optionally determined by one or more of the foregoing markers or observations.

There are also basically two types of bone—cortical and trabecular—that define the outer and inner volumes of bone respectively. Another important discovery by these inventors is the ability of genistein, when present in the combined dosage forms described herein, to support and promote the health of both types of bone architecture, as determined by visual observation and analysis of the bone structure for, for example, thickness of cortical bone structure and restoration of cross-linking is trabecular bone. Therefore, in yet another embodiment, the invention provides a method of providing genistein and vitamin D3 supplementation to a host in need thereof, comprising orally administering genistein and vitamin D3, wherein the ratio of genistein to vitamin D3 results in an improvement in bone health as measured by improvements in cortical and trabecular bone structure.

The invention also provides methods of supplementation and combination dosage forms that combine the beneficial effects of genistein with zinc. Based upon this need, the inventors have developed a novel combination of genistein and chelated zinc, referred to herein as citrated zinc glycinate, having the chemical formula $(ZnCitrate_n Gly_m)$, wherein n and m are each greater than 0.01, and n+m ranges from 2 to 4. In one embodiment, the invention provides a method of supplementing the diet with genistein and zinc comprising administering on a daily basis to a host in need thereof citrated zinc glycinate and approximately 54 mg of genistein. In another embodiment the invention provides a combination dosage form comprising citrated zinc glycinate and genistein in an amount of approximately 54 mg when administered daily, or a combination dosage form comprising citrated zinc glycinate and genistein in an amount of approximately 27 mg when administered twice daily (b.i.d.). As with the genistein and vitamin D3 combination, these combinations of genistein and zinc also preferably (1) favour new bone formation over the inhibition of bone resorption, and (2) promotes the health of trabecular and cortical bone structure. The weight ratio of genistein to zinc (elemental) preferably ranges from about 4:1 to about 15:1, more preferably ranges from about 5:1 to about 10:1, and most preferably ranges from about 6.0 to about 7.5.

In a most preferred embodiment, the invention provides a three component dosage form that includes the benefits of genistein, vitamin D3 and zinc and which, in the preferred ratios described herein, preferably also (1) favours new bone formation over the inhibition of bone resorption, and (2) promotes the health of trabecular and cortical bone structure. Therefore, in still another embodiment, the invention provides a method of vitamin supplementation for supporting and promoting the health of bone in a patient in need thereof, comprising orally administering on a daily basis any of the formulations of the present invention, but most preferably:

a) about 54 mg of genistein aglycone;
    b) about 200 IU of vitamin D3; and
    c) about 8 mg of zinc.

Additional advantages and aspects of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

FIGURES

FIG. 1 is a series of four bar graphs depicting changes in biochemical markers of bone resorption [soluble receptor activator of nuclear factor kappaB ligand (sRANKL) and C-terminal telopeptide (CTX)] and formation [bone-specific alkaline phosphatase and osteoprotegerin (OPG)], in animals treated with 0-1000 mg/day human dose equivalents of genistein, with and without calcium and vitamin D3 supplementation.

DESCRIPTION OF THE INVENTION

Definitions

Figure 1:
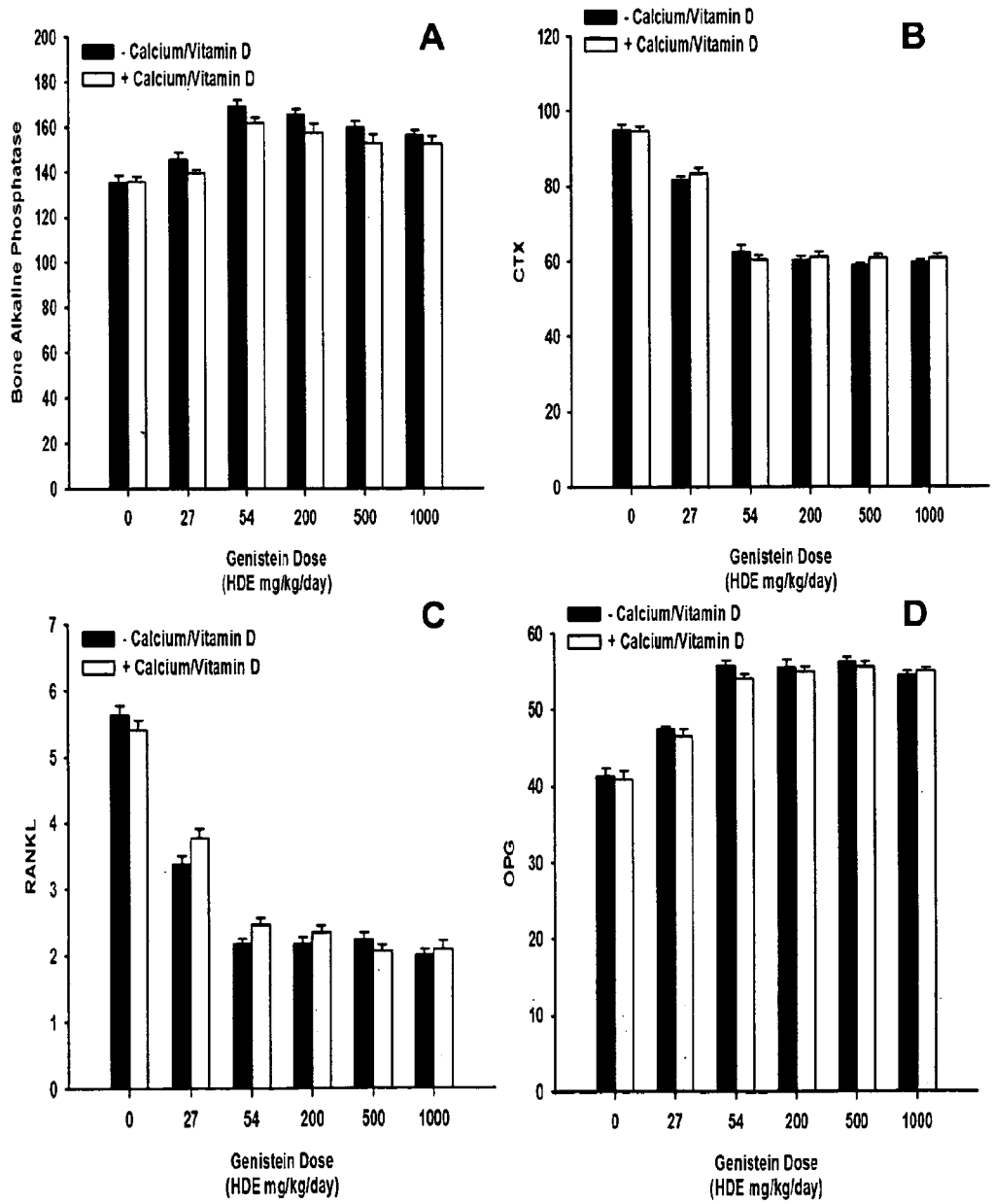

As used in this specification and in the claims which follow, the singular forms "a," "an" and "the" include plural referents unless the context clearly dictates otherwise. Thus, for example, reference to "an ingredient" includes mixtures of ingredients, reference to "an active pharmaceutical agent" includes more than one active pharmaceutical agent, and the like.

"Treating" or "treatment" of a disease includes (1) preventing the disease from occurring in an animal that may be predisposed to the disease but does not yet experience or display symptoms of the disease, (2) inhibiting the disease, i.e. arresting its development, or (3) relieving the disease, i.e. causing regression of the disease. In addition, treatment can include supporting particular conditions of health, or providing dietary supplementation of nutritionally active ingredients.

"Genistein" is chemically named 4',5,7-trihydroxyisoflavone, and has the following chemical structure:

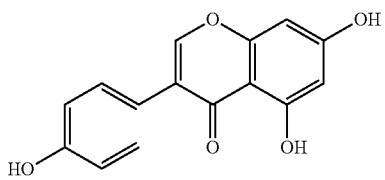 [SMILES: C=C/C(O)=C\C=C\c1coc2cc(O)cc(O)c2c1=O]

The compound is derived from natural soy products in low amounts, and in its natural form, is conjugated to a glucoside group and is termed genistin. In a preferred form for this invention, the molecule is present almost entirely as an unconjugated base, preferably having a purity of greater than 96, 97 or 98 wt. %, and is referred to as genistein aglycone.

Throughout this document the amount of genistein to be administered on a daily basis is 54 mg. It will be understood that other amounts can be administered as long as they provide a therapeutically effective dose. A therapeutically effective amount of genistein refers to an amount of genistein capable of improving bone mineral density in post-menopausal female patients, or other biochemical markers of bone formation or reduced bone resorption. The amount preferably ranges from about 45 to about 70 mg per day, or from about 50 to about 60 mg per day, in any of the embodiments described herein.

Citrated zinc glycinate refers to a chelated/salt form of zinc having the following chemical structure: $ZnCitrate_nGly_m$, wherein each of n and m are greater than 0.01, and n+m ranges from about 2 to about 4. In preferred embodiments: n+m ranges from about 2 to about 3 or from about 2 to about 2.5; n ranges from about 0.01 to about 1 or from about 0.1 to about 0.5; and m ranges from about 1 to about 4, from about 1.5 to about 3, or from about 1.75 to about 2.5.

The term "aglycone equivalent" is often used to describe the genistein molecule, and refers to the amount of genistein base present excluding any glucoside conjugates or other isoflavones. In like manner, the term "elemental equivalent" is often used to describe chelated zinc, and refers to the amount of elemental zinc present in the chelate, without regard to the amount of chelating agent present.

Any of the active ingredients herein may be administered as pharmaceutically acceptable salts where chemically feasible. "Pharmaceutically acceptable salts" means salts which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

In addition, pharmaceutically acceptable salts may be formed when an acidic proton present is capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. Pharmaceutically acceptable salts also include chelated forms of metallic compounds, such as those based on amino acids such as arginine and glycine.

A dosage form, as used herein, refers to a formulation that is ready for administration to a subject. As used herein, it may refer to solid dosage forms, including, but not limited to, tablets, powders and capsules. Alternatively, it may refer to a liquid dosage form such as a solution or a suspension.

The term "about" or "ca." accommodates industry standards for dietary supplements, medical foods and pharmaceuticals that allow for some level of variability within and among dosage forms and active ingredients. Thus, for example, a product that contains X mg of an active ingredient may contain a greater or lesser amount of ingredient X, to accommodate the imprecision associated with manufacturing processes, product degradation, and purity and potency variations in raw material supplies. In various embodiment, the term "about" accommodates variability in the active ingredient amounts of up to 50%, 25%, 10%, 5%, 3% or 2% (plus or minus).

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Therapeutically effective amount," unless stated to the contrary herein, means that amount which, when administered to an animal for treating a disease or supporting a metabolic process, is sufficient to effect such treatment for the disease, or to support the metabolic process.

Weight percentages are given in terms of the element described. Therefore, a composition that contains 4 mg of zinc chelated by an amino acid would contain greater than 4 mg of the salt, but only 4 mg of elemental zinc ion.

DISCUSSION

In a first embodiment the invention provides a method of providing genistein and vitamin D3 supplementation, without decreasing the efficacy of the genistein, comprising administering on a daily basis to a host in need thereof (a) about 54 mg of genistein aglycone; and (b) from about 200 to about 1000 IU of vitamin D3. In like manner, the invention provides a daily oral dosage form, preferably in the form of a capsule or tablet, that comprises (a) about 54 mg of genistein aglycone; and (b) from about 200 to about 1000 IU of vitamin D3. These quantities can be divided in half to provide a b.i.d. dosing form and dosing regimen that includes (a) about 27 mg of genistein aglycone; and (b) from about 100 to about 500 IU of vitamin D3.

The gensitein aglycone is administered in therapeutically effective amounts, and is preferably administered in an amount of approximately 54 mg per day, preferably in two equal doses. Other doses may also be employed ranging from about 40 to about 150 or from about 45 to about 80 or 100 mg per day or from about 50 to about 60 mg per day, again preferably in two equal doses.

The vitamin D3 is preferably administered in a therapeutically effective amount, meaning an amount of vitamin D3 that is capable of restoring population norm serum vitamin D3 levels in patients moderately deficient in vitamin D3 (typically regarded as about 70 nmol/L). It is known that other related molecules also yield vitamin D3 in vivo when ingested, and in another embodiment the vitamin D3 supplementation is furnished by administering one of these related molecules, which are herein referred to as "means for providing vitamin D3 supplementation."

The therapeutically effective amount of vitamin D3 preferably ranges from about 100 to about 1500 or 2000 IU/day, more preferably ranges from about 200 to about 1000 IU/day, and most preferably ranges from about 400 to about 800 IU/day, with a daily dose of 400 IU being most preferred. Once again, these amounts may be present in a single dosage unit, but preferably are divided into two daily BID doses.

In alternative embodiments, the therapeutically effective amount of vitamin D3 preferably ranges from about 1000 to about 3500 IU/day, and more preferably ranges from about 2000 to about 3000 IU/day. Once again, these amounts may be present in a single dosage unit, but preferably are divided into two daily BID doses.

The dosing regimen or dosage form may further comprise the administration of zinc, which is preferably administered on a daily basis in a therapeutically effective amount. A therapeutically effective amount of zinc refers to an amount of zinc that is effective to improve bone mineral density in a post-menopausal female patient, or other biochemical markers of bone formation or reduced bone resorption. Therapeutic amounts of zinc, based on the amount of elemental zinc present in a salt when a salt is employed, on a daily basis, range from about 2 to about 50 mg, more preferably from about 5 to about 20 mg, still more preferably from about 6 to about 10 mg, and most preferably about 8 mg. Once again, these amounts may be present in a unitary dosage form, or may preferably be divided into two daily BID doses.

The zinc can be present in elemental form or in any acceptable salt form thereof, but is preferably present as zinc sulphate, zinc bisglycinate, or another chelated form of zinc such as citrated zinc glycinate. Alternative amino acids with which the zinc can be chelated include alanine, arginine, asparagines, aspartic acid, cysteine, glutamine, glutamic acid, glycine, histidine, isoleucine, leucine, lysine, methionine, phenylalanine, praline, serine, threonine, tryptophan, tyrosine, valine, and synthetic analogs and derivatives thereof. A preferred structure for citrated zinc bisglycinate is:

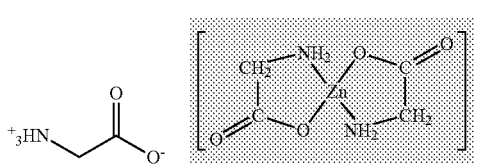

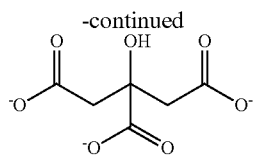

This compound is assigned CAS registry number 955009-96-8.

In another embodiment the invention provides a method of providing genistein and zinc supplementation comprising administering on a daily basis to a host in need thereof (a) about 54 mg of genistein aglycone; and (b) a therapeutically effective amount of zinc, preferably from about 2 to about 40 mg of zinc as $ZnCitrate_nGly_m$ (zinc equivalent), wherein each of n and m are greater than 0.01, and n+m ranges from about 2 to about 4. In like manner, the invention provides a daily oral dosage form, preferably in the form of a capsule or tablet, that comprises (a) about 54 mg of genistein aglycone; and (b) a therapeutically effective amount of zinc, preferably from about 2 to about 40 mg of zinc as $ZnCitrate_nGly_m$ (zinc equivalent), wherein each of n and m are greater than 0.01, and n+m ranges from about 2 to about 4. It will be understood that these quantities can be divided in half to provide a b.i.d. dosing form and dosing regimen that includes (a) about 27 mg of genistein aglycone; and (b) from about 1 to about 20 mg of zinc as $ZnCitrate_nGly_m$ (zinc equivalent).

Therapeutic amounts of citrated zinc glycinate, based on the amount of elemental zinc present in a salt when a salt is employed, on a daily basis, range from about 2 to about 50 mg, more preferably from about 5 to about 20 mg, still more preferably from about 6 to about 10 mg, and most preferably about 8 mg. Once again, these amounts may be present in a unitary dosage form, or may be preferably divided into two daily BID doses (i.e. in amounts ranging from 1 to 25 mg, 2.5 to 10 mg, 3 to 5 mg, or 4 mg).

In another embodiment, vitamin D3 is administered along with the genistein/$ZnCitrate_nGly_m$ combination, preferably in a therapeutically effective amount (as defined above). The therapeutically effective amount of vitamin D3 preferably ranges from about 100 to about 1500 or 2000 IU/day, more preferably ranges from about 200 to about 1000 IU/day, and most preferably ranges from about 400 to about 800 IU/day, with a daily dose of 400 IU being most preferred. Once again, these amounts may be present in a single dosage unit, but preferably are divided into two daily BID doses (i.e. as single doses of from 200 to 400 IU with 200 IU most preferred).

It will be understood that the invention is not particularly limited by these amounts of active ingredients used in the therapy, and can be practiced with any therapeutically effective amounts of active ingredients. Therefore, in a broader sense the invention provides a method of supporting human health comprising orally administering to a human subject therapeutically effective amounts of genistein and vitamin D3, or genistein and zinc. The invention also provides an oral dosage form comprising therapeutically effective amounts of genistein and vitamin D3, or genistein and zinc.

The invention also allows for the intake or administration of other dietary ingredients in combination with the genistein. Calcium is especially preferred, and should be administered in an amount sufficient to restore or maintain serum calcium levels at an accepted population norm for calcium (typically regarded as about 8.5 to 10.2 mg/dL). The calcium may be administered as part of the normal diet, or may be administered as part of a separate dietary supplement. In the latter case, the calcium may be included in the genistein dosage form, or may be included in a separate oral dosage form. When administered as part of a dietary supplement, above, and beyond the normal amounts ingested in the diet, the amount of calcium preferably ranges from about 200 to about 2000 mg/day, from about 400 to about 1500 mg/day, or from about 800 to about 1200 mg/day, most preferably about 1000 mg/day. These quantities can be ingested in a single dosage form, or may be divided into BID doses, in which case the amount of calcium in each dose would preferably range from 100 to 100 mg, from 200 to 750 mg, from 400 to 600 mg, or about 500 mg.

In one particular embodiment, the invention provides for the use of the citrated zinc glycinate in other methods and dosage forms, generally in the therapeutically effective amounts described above, and optionally in combination with other active ingredients in the therapeutically effective amounts described herein. Thus, in another embodiment the invention provides a method for supporting bone health comprising administering a pharmaceutical composition comprising a therapeutically effective amount of $ZnCitrate_nGly_m$, wherein each of n and m are greater than 0.01, and n+m ranges from about 2 to about 4. In another embodiment the invention provides a solid oral dosage form that comprises a therapeutically effective amount of $ZnCitrate_nGly_m$ and a pharmaceutically acceptable excipient, wherein each of n and m are greater than 0.01, and n+m ranges from about 2 to about 4.

Pharmaceutical Compositions

Various pharmaceutical compositions can be developed that make use of the combinations described herein, but the composition is preferably administered orally in liquid or solid form. These compositions will generally include an inert diluent or an edible carrier. They may be enclosed in gelatin capsules (for oral use) or compressed into tablets (for oral or buccal use) or formulated into troches (for buccal use). For these purposes, the active compound can be incorporated with excipients and used in the form of tablets, troches, or capsules. Pharmaceutically compatible binding agents, and/or adjuvant materials can be included as part of the composition.

Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, orally disintegrating film, orally disintegrating tablet, chewing gum or the like. A syrup may contain, in addition to the active compounds, sucrose as a sweetening agent and certain preservatives, dyes and colorings and flavors.

Methods of Treatment

In still further embodiments, the invention provides methods of treating various disease states, or of supporting conditions of health, using the combinations of the present invention. Disease states that the combinations may be used to manage include:
  Osteopenia
  osteoporosis,
  osteitis deformans (Paget's disease of bone),
  bone metastasis (with or without hypercalcemia),
  multiple myeloma, and
  other conditions that feature bone fragility.

Healthy conditions that the combinations may be used to support include:
  bone health, and
  post-menopausal health.

The method has particular use in the field of bone health, and the effectiveness of the combinations can be gauged based on their ability to influence various metabolic processes affecting bone health. For example, it has been discovered that the methods can improve both trabecular and cortical bone architecture, as described in the examples given below. It has also been discovered that the methods can improve bone health by increasing the rate of bone formation (by supporting osteoblast activity), while at the same time decreasing the rate of bone resorption (by inhibiting osteoclast activity). In a preferred embodiment the methods are practiced so that bone mineral density is improved through metabolic processes that favor bone formation over the inhibition of bone resorption.

EXAMPLES

Example 1

Genistein Dose-Ranging Preclinical Study

This study was carried out to evaluate the effects of different human dose equivalents of genistein (aglycone) alone, or in combination with supplemental calcium carbonate and vitamin D3, on bone density, markers, and histology in ovariectomized rats. Forty-eight three month old ovariectomized (OVX) female Sprague-Dawley rats were purchased from Charles River Laboratories. Animals were maintained in plastic cages under standard environmental conditions with water and standard rat chow available ad libitum at the Animal Facility of the Department of Clinical and Experimental Medicine and Pharmacology of the University of Messina, Messina, Italy. After 1 week of acclimation, animals were randomly assigned to 12 different treatment groups that lasted for 6 weeks as summarized in Table 1 below:

TABLE 1

Genistein Dose Titration Group Designations

| Group | Number of Animals | Genistein Dose (mg/kg/day) | Genistein Human Dose Equivalents (mg/day)) | Supplemental Calcium and vitamin D3 |
|---|---|---|---|---|
| 1 | 4 | 0 | 0 | |
| 2 | | | | ✓ |
| 3 | | 2.38 | 27 | |
| 4 | | | | ✓ |
| 5 | | 4.76 | 54 | |
| 6 | | | | ✓ |
| 7 | | 17.63 | 200 | |
| 8 | | | | ✓ |
| 9 | | 44.09 | 500 | |

TABLE 1-continued

Genistein Dose Titration Group Designations

| Group | Number of Animals | Genistein Dose (mg/kg/day) | Genistein Human Dose Equivalents (mg/day)) | Supplemental Calcium and vitamin D3 |
|---|---|---|---|---|
| 10 | | | | ✓ |
| 11 | | 88.18 | 1000 | |
| 12 | | | | ✓ |

Genistein doses were converted into human equivalents by using the following formula: (human dose in mg/m$^2$)=(kin)×(dose in mg/kg) where human m$^2$ for a woman of 60 kg (considered as a medium weight for our cohort of post-menopausal women) is 1.62 and km is the conversion factor (for a rat of 250 gr is 7.0) {Freireich, 1966 4611/id. Genistein was diluted in a 1:1 solution of 0.9% NaCl and DMSO and administered by intraperitoneal injection. Animals received 50% supplementation of their normal daily intake of calcium and vitamin D3 (50.4 IU/kg/day) by oral gavage, which equated to 366.52 mg/kg/day of calcium and 50.4 IU/kg/day of vitamin D3.

Bone mineral density of the right femur was measured using dual-energy X-ray absorptiometry. The coefficient of variation for femur BMD was 1.16%. Animals were maintained under controlled conditions for 6 weeks, at the end of the experiments were sacrificed under general anaesthesia (with chloral hydrate 400 mg/kg/ip) after blood collection by cardiac puncture. Blood was centrifuged and serum stored immediately at −20° C. for analysis. Serum was used to quantify markers of bone resorption [soluble receptor activator of nuclear factor kappaB ligand (sRANKL) and C-terminal telopeptide (CTX)] and formation [bone-specific alkaline phosphatase and osteoprotegerin (OPG)].

Figure 2:
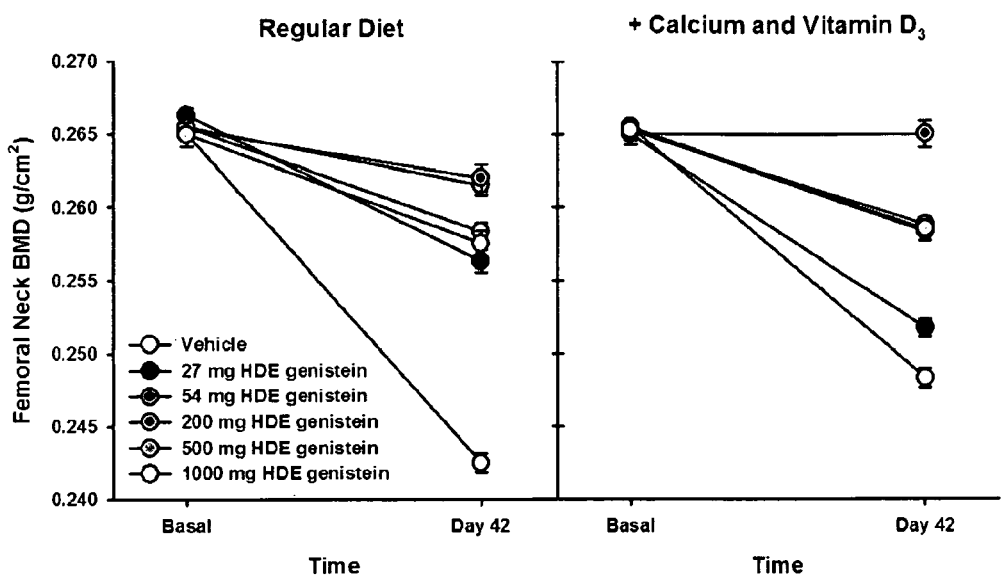
FIG. 2 is a graph showing the change in femoral neck bone mineral density over a 42 day course of treatment in animals treated with 0-1000 mg/day human equivalent of genistein, with and without calcium and vitamin D3 supplementation.
Figure 3:
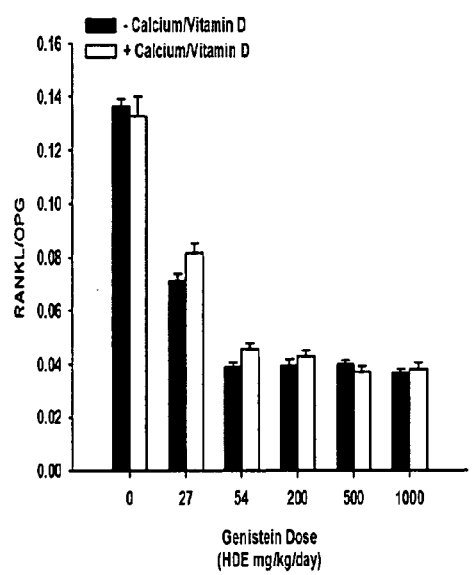
FIG. 3 is a bar graph depicting the RANKL/OPG ratio in animals treated with 0-1000 mg/day human dose equivalents of genistein, with and without calcium and vitamin D3 supplementation, suggesting that the combination favourably rebalances bone metabolism in favour of formation, rather than resorption.

Gensitein significantly (all p<0.001; FIG. 1) and dose-dependently increased markers of bone formation (Bone specific alkaline phosphatase and osteoprotegerin) and decreased markers of bone resorption (CTX and sRANKL), and showed increases in bone mineral density (p<0.001; FIG. 2). Genistein decreased the RANKL/OPG ratio (p<0.001; FIG. 3) suggesting that it favourably rebalances bone metabolism in favour of formation, rather than resorption. In each case, the genistein effect reached a plateau at 54 mg human dose equivalent and showed no further significant improvement beyond this dose as determined by post-hoc testing. N.B. All data are expressed as mean+S.E.M. Units for each marker are as follows: A) Units/L, B) ng/ml, C) pmol/L, D) pmol/L.

Supplemental calcium and vitamin D3 had no effect on levels of any bone marker with the exception of bone-alkaline phosphatase, which was significantly (p=0.004) decreased by calcium and vitamin D3 independent of genistein dose. Interestingly, there was a significant three-way interaction between time, genistein, and calcium/vitamin D3 treatment (p<0.001), when bone mineral density was evaluated. Animals treated with the 27, 200, 500 and 1,000 mg doses showed no improvement in BMD when supplemented with vitamin D3 or calcium, and even worsened in some instances. Animals treated with the equivalent of 54 mg genistein per day are the only ones that showed a statistically significant preservation in BMD when supplemented with vitamin D3 and calcium. Genistein produced significant increases in BMD over 6 weeks in calcium and vitamin D3-replete rats at 54 mg/day and above, with no additional therapeutic benefit observed at doses greater than 54 mg human dose equivalents per day.

Example 2

Genistein Bone Architecture Study

Three month old ovariectomized (OVX) female Sprague-Dawley rats were purchased from Charles River Laboratories. Animals were maintained in plastic cages under standard environmental conditions with water and standard rat chow available ad libitum at the Animal Facility of the Department of Clinical and Experimental Medicine and Pharmacology of the University of Messina, Messina, Italy.

Dose Calculation—Genistein doses were converted into animal equivalents by using the following formula: (human dose in mg/m$^2$)=(km)×(dose in mg/kg) where human m$^2$ for a woman of 60 kg (considered as a medium weight for our cohort of post-menopausal women) is 1.62 and km is the conversion factor (for a rat of 250 gr is 7.0) {Freireich, 1966 4611/id}. Therefore, animals given the human equivalent of 54 mg/day were administered 4.76 mg/kg/day. Genistein was diluted in a 1:1 solution of 0.9% NaCl and DMSO and administered by intraperitoneal injection in a volume of 100:1.

Histology—Rat femora decalcified in 4% EDTA for approximately 1 week and then processed for routine paraffin embedding following standard procedures. Sections were cut at the femoral head just proximal to the coxofemoral joint and stained with hematoxylin and eosin.

Results—Photomicrographs of the bone show that, as expected, ovariectomy led to marked trabecular bone loss in the femoral head compared to an animal that received sham surgery. The photomicrographs also show preliminary evidence that genistein given at a human equivalent dose of 54 mg/day restores trabecular architecture (trabecular rod number and thickness) to approximately that of an animal that did not undergo ovariectomy-induced bone loss. Therefore, genistein may preserve trabecular bone matrix lost due to ovarian hormone depletion, in addition to cortical bone structure.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of providing genistein and vitamin D3 supplementation to a host in need thereof, so that the effectiveness of the genistein is not compromised, comprising orally administering on a daily basis:
 a) about 54 mg of genistein aglycone;
 b) a quantity of vitamin D3 that is effective to provide vitamin D3 supplementation, but which does not compromise the effectiveness of the genistein, consisting of from about 200 to about 1000 IU of vitamin D3; and
 c) a therapeutically effective amount of calcium.

2. The method of claim 1 wherein said genistein and vitamin D3 are administered in a ratio that favors new bone formation over the inhibition of bone resorption.

3. The method of claim 1 wherein said genistein and vitamin D3 are administered in a ratio that promotes the health of trabecular and cortical bone architecture.

4. The method of claim 1 comprising administering about 400 IU of vitamin D3 on a daily basis.

5. The method of claim 1 further comprising administering from about 2 to about 40 mg of zinc.

6. The method of claim 5 wherein said genistein and zinc are administered in a ratio that favors new bone formation over the inhibition of bone resorption.

7. The method of claim 5 wherein said genistein and zinc are administered in a ratio that promotes the health of trabecular and cortical bone architecture.

8. The method of claim 1 comprising administering about 400 IU of vitamin D3, and further comprising administering about 8 mg of zinc as $ZnCitrate_n Gly_m$ (zinc equivalent), wherein each of n and m are greater than 0.01, and n+m ranges from about 2 to about 4, in the form of a tablet or capsule.

9. The method of claim 1, further comprising administering a therapeutically effective amount of calcium.

* * * * *